(12) United States Patent
Lambert

(10) Patent No.: US 9,303,067 B2
(45) Date of Patent: Apr. 5, 2016

(54) SUSTAINED RELEASE FORMULATION COMPRISING A SOMATOSTATIN ANALOGUE

(71) Applicant: Olivier Lambert, Spechbach-le-Haut (FR)

(72) Inventor: Olivier Lambert, Spechbach-le-Haut (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/265,605

(22) Filed: Apr. 30, 2014

(65) Prior Publication Data
US 2015/0038414 A1  Feb. 5, 2015

Related U.S. Application Data

(63) Continuation of application No. 11/721,082, filed as application No. PCT/EP2005/013703 on Dec. 20, 2005, now abandoned.

(30) Foreign Application Priority Data

Dec. 21, 2004 (GB) .................................. 0428151.5

(51) Int. Cl.
| *C07K 7/08* | (2006.01) |
| *A61K 9/00* | (2006.01) |
| *A61K 38/10* | (2006.01) |
| *A61K 9/08* | (2006.01) |

(52) U.S. Cl.
CPC ................. *C07K 7/08* (2013.01); *A61K 9/0019* (2013.01); *A61K 38/10* (2013.01); *A61K 9/08* (2013.01)

(58) Field of Classification Search
None
See application file for complete search history.

(56) References Cited

U.S. PATENT DOCUMENTS

| 4,603,120 | A | 7/1986 | Kamber |
| 5,595,760 | A | 1/1997 | Cherif-Cheikh |
| 5,639,480 | A | 6/1997 | Bodmer et al. |
| 6,503,534 | B1 | 1/2003 | Pellet et al. |
| 2002/0111603 | A1 | 8/2002 | Cheikh |
| 2003/0044463 | A1* | 3/2003 | Deghenghi et al. ........... 424/468 |

FOREIGN PATENT DOCUMENTS

| EP | 1475114 B1 | 11/2006 |
| EP | 2 310 042 B | * 5/2012 |
| WO | 96/07398 | 3/1996 |
| WO | 98/27962 | 7/1998 |
| WO | 02/10192 | 2/2002 |
| WO | 03/075887 A1 | 9/2003 |
| WO | 2004/060391 | 7/2004 |

OTHER PUBLICATIONS

DrugBank (accessed Jul. 8, 2015).*
Caron et al. (Efficacy of the New-ling acting Formulation of Lanreotide in the Management of Acromegaly; The Journal of Clinical Endocrinology and Metabolism; 87(1) 99-104) 2002.*
Caron Ph. et al., 2004, Clinical Endocrinology, 60: 734-740.
Caron Philippe et al., 2007, Therapy, 4(1)9-29.
Astruc Beatrice et al, 2005, Journal of Clinical Pharmacology, 45:836-844.
Caron PH. et al., 2002, Th. Journal of Clinical Endocrinology & Metabolism, 87 (1); 99-104.
Jang Sun Woo et al., "Stability of octastatin a somatostatin analog cyclic octapeptide in aqueous solution", Pharmaceutical Development and Technology, vol. 2, No. 4, pp. 409-414, 1997.

* cited by examiner

*Primary Examiner* — James H Alstrum Acevedo
*Assistant Examiner* — Tara Martinez
(74) *Attorney, Agent, or Firm* — Michelle Han

(57) ABSTRACT

A pharmaceutical composition for parenteral administration of a somatostatin analog salt of aspartate, e.g. mono- or diaspartate, lactate, succinate, e.g. mono- or disuccinate, acetate, glutamate, e.g. mono- or diglutamate or citrate and water forming a gelling depot system after injection in contact with the body fluid.

16 Claims, 2 Drawing Sheets

SUSTAINED RELEASE FORMULATION COMPRISING A SOMATOSTATIN ANALOGUE

The present invention relates to liquid pharmaceutical compositions, in particular to depot formulations comprising somatostatin analogues and to a process for preparing said depot formulations.

Figure 1:
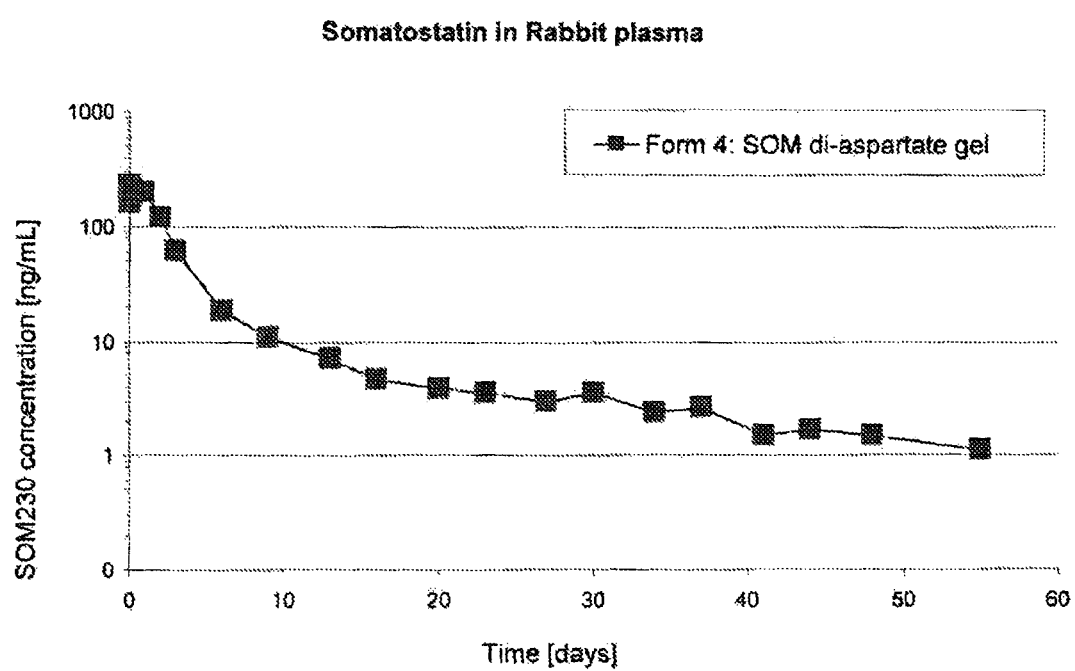
FIG. 1 shows release profile in rabbits of the drug product having the composition given in example 1.

Depot formulations are typically administered parenterally. Somatostatin depot formulations may be administered by injection subcutaneously or intramuscularly through a small gauge needle or placed into accessible tissue sites through a cannula. However parenteral administration may be very painful especially if repeated injections are necessary. Furthermore, there may be difficulties with depot formulations which are administered in liquid form and which form a solid implant in the body after injection. Often the solidifying process starts in the syringe before injection and causes needle clogging.

Further, these depot formulations may comprise a polymer or a mixture of polymers that has to be dissolved in an organic solvent, e.g. they may comprise more than 50% of an organic solvent. If the organic solvent remains in the solution for injection it might cause severe tissue irritation or necrosis at the site of implantation.

EP 779 805 provides a pharmaceutical composition consisting of a soluble peptide salt which will form a get upon contact with a body fluid, and up to 30% by weight of the composition of a pharmaceutically acceptable carrier. The peptides described in EP 779805 are somatostatins or a somatostatin analogs, e.g. lanreotide.

Surprisingly it has now been found that advantageous parenteral somatostatin depot formulations may be obtained with a composition comprising a salt of a somatostatin analogue and water having a pH from 3 to 7 without using a polymer and without using an organic solvent.

The present invention provides in one aspect a pharmaceutical composition for parenteral administration comprising a somatostatin analogue salt of aspartate, e.g. mono- or diaspartate, glutamate, e.g. mono- or diglutamate, or succinate, e.g. mono- or disuccinate, lactate, acetate or citrate and water, forming a gelling depot after injection in contact with body fluid. The salt:base ratio of the somatostatin analogue salts may range from 0.1 to 2 and provides the solubility of the somatostatin analogue salt. The pharmaceutical composition has a pH between about 3.0 and 7.0, preferably from between 4.0 and 6.0 and more preferably from between about 4.0 and 5.0. Optionally the composition may comprise a pharmaceutically acceptable buffer in an amount to stabilize the pH between about 3.0 and 7.0, preferably between about 4.0 and 6.0, most preferably between 4.0 and 5.0.

In another aspect the present invention provides a pharmaceutical composition for parenteral administration comprising a somatostatin analogue salt of aspartate, e.g. mono- or diaspartate, glutamate, e.g. mono- or diglutamate, lactate, succinate, e.g. mono- or disuccinate, acetate or citrate, and water, having a pH between about 3.0 and 7.0, forming a gelling depot after injection in contact with body fluid.

The composition having a pH between about 3.0 and 7.0 provides good solubility and therefore the composition of the invention may be stored over an extended period of time without precipitation. The composition is administered to the patient by injection wherein the composition will start to form a gelling depot after and not before interaction with patients body fluid. The gelling depot releases the somatostatin analogue salt of aspartate, lactate, succinate, acetate, glutamate or citrate within the patient over an extended period of time.

In another aspect the invention provides a process for preparing a depot formulation by i) dissolving a somatostatin analogue salt of aspartate, e.g. mono- or diaspartate, lactate, succinate, e.g. mono- or disuccinate, acetate, glutamate, e.g. mono- or diglutamate or citrate in water, ii) optionally adding a buffer to stabilize the pH of the solution, and optionally iii) filling the solution into a syringe In a further aspect the invention provides a process for preparing a depot formulation by i) dissolving a somatostatin analogue salt of aspartate, e.g. mono- or diaspartate, lactate, succinate, e.g. mono- or disuccinate, acetate, glutamate, e.g. mono- or diglutamate, or citrate in water, having a pH of between 3.0 and 7.0, ii) optionally adding a buffer to stabilize the pH of the solution, and optionally iii) filling the solution into a syringe The present invention relates to somatostatin analogue salts of aspartate, e.g. mono- or diaspartate, lactate, succinate, e.g. mono- or disuccinate, acetate, glutamate, e.g. mono- or diglutamate or citrate.

Somatostatin is a tetradecapeptide having the structure

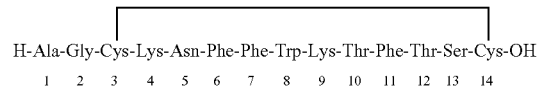

Somatostatin analogues of particular interest have been described e.g. In WO 97/01579 and WO 97/25977. Said somatostatin analogues comprise the amino acid sequence of formula I

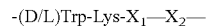

wherein $X_1$ is a radical of formula (a) or (b)

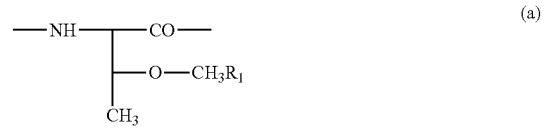

wherein R₁ is optionally substituted phenyl, wherein the substituent may be halogen, methyl, ethyl, methoxy or ethoxy, R₂ is —Z—CH₂—R₁, —CH₂—CO—O—CH₂—R₁,

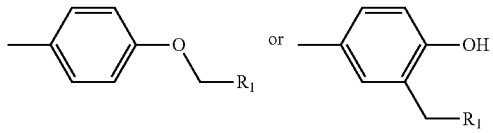

wherein Z₁ is O or S, and

X₂ is an α-amino acid having an aromatic residue on the C_α side chain, or an amino acid unit selected from Dab, Dpr, Dpm, His, (Bzl)HyPro, thienyl-Ala cyclohexyl-Ala and t-butyl-Ala, the residue Lys of said sequence corresponding to the residue Lys⁹ of the native somatostatin-14.

By somatostatin analogue as used herein is meant a straight-chain or cyclic peptide derived from that of the naturally occurring somatostatin-14, comprising the sequence of formula I and wherein additionally one or more amino acid units have been omitted and/or replaced by one or more other amino acid radical(s) and/or wherein one or more functional groups have been replaced by one or more other functional groups and/or one or more groups have been replaced by one or several other isosteric groups. In general the term covers all modified derivatives of the native somatostatin-14 comprising the above sequence of formula I which have binding affinity in the nM range to at least one somatostatin receptor subtype as defined hereinafter.

Preferably, the somatostatin analogue is a compound in which the residues at positions 8 through 11 of the somatostatin-14 are represented by the sequence of formula I as defined above.

More preferably, the somatostatin analogue is a compound as disclosed above comprising a hexapeptide unit, the residues at positions 3 through 6 of said hexapeptide unit comprising the sequence of formula I. Particularly preferred is a somatostatin hexapeptide wherein the residues at positions 1 and 2 of the hexapeptide unit may be any of those as known in the art, e.g. as disclosed by A. S. Dutta in Small Peptides, Vol. 19, 292-354, Elsevier, 1993, or as substituents for, Phe⁶ and/or Phe⁷ of sornatostatin-14.

More particularly the somatostatin analogue is a compound in which the hexapeptide unit is cyclic, e.g. having a direct peptide linkage between the α-carbonyl group of the residue at position 6 and the α-amino group of the residue at position 1.

While Lys, X₁ and X₂ in the sequence of formula I have the L-configuration, Trp may have the D- or L-configuration. Preferably Trp has the D-configuration.

X₁ is preferably a residue of formula (a) or (b), R₂ being preferably

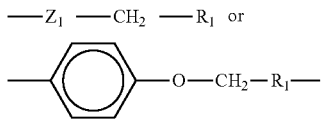

When X₂ comprises an aromatic residue on the C_α side chain, it may suitably be a natural or unnatural α-amino acid, e.g. Phe, Tyr, Trp, Nal, Pal, benzothienyl-Ala, Tic and thyronin, preferably Phe or Nal, more preferably Phe. X₂ is preferably an α-amino acid bearing an aromatic residue on the C_α side chain.

When R₁ is substituted phenyl, it may suitably be substituted by halogen, methyl, ethyl, methoxy or ethoxy e.g. in ortho and/or para. More preferably R₁ is unsubstituted phenyl.

Z₁ is preferably O.

Representative compounds of the invention are e.g. compounds of formula (II)

$$\text{cyclo(A-ZZ}_a\text{-(D/L)Trp-Lys-X}_1\text{-X}_2\text{)}\quad\text{(II)}$$
$$\quad\quad 1\quad 2\quad\quad\quad\quad 3\quad\quad 4\quad\; 5\quad 6$$

wherein

X₁ and X₂ are as defined above,

A is a divalent residue selected from Pro,

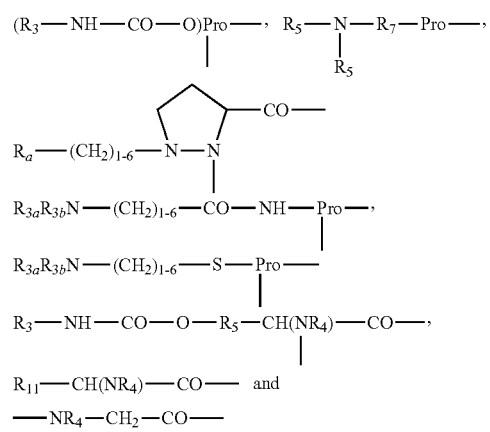

wherein R₃ is NR₈R₉—C₂₋₆alkylene, guanidino-C₂₋₆alkylene or C₂₋₆lkylene-COOH, R₃ₐ is H, C₁₋₄alkyl or has independently one of the significances given for R₃, R₃_b is H or C₁₋₄alkyl, R_a is OH or NR₅R₆, R_b, is —(CH₂)₁₋₃— or —CH(CH₃)—, R₄ is H or CH₃, R₄ₐ is optionally ring-substituted benzyl, each of R₅ and R₆ independently is H, C₁₋₄alkyl, ω-amino-C₁₋₄alkylene, ω-hydroxy-C₁₋₄alkylene or acyl, R₇ is a direct bond or C₁₋₆alkylene, each of R₈ and R₉ independently is H, C₁₋₄alkyl, ω-hydroxy-C₂₋₄alkylene, acyl or CH₂OH—(CHOH)_c—CH₂— wherein c is 0, 1, 2, 3 or 4, or R₈ and R₉ form together with the nitrogen atom to which they are attached a heterocyclic group which may comprise a further heteroatom, and R₁₁ is optionally ring-substituted benzyl, —(CH₂)₁₋₃—OH, CH₃—CH(OH)— or —(CH₂)₁₋₅—NR₅R₆, and ZZ_a is a natural or unnatural α-amino acid unit.

ZZ_a may have the D- or L-configuration. When ZZ_a is a natural or unnatural α-amino acid unit, it may suitably be e.g. Thr, Ser, Ala, Val, Ile, Leu, Nle, His, Arg, Lys, Nal, Pal, Tyr, Trp, optionally ring-substituted Phe or N^α-benzyl-Gly. When ZZ_a is Phe, the benzene ring thereof may be substituted by e.g. NH₂, NO₂, CH₃, OCH₃ or halogen, preferably in para position. When ZZ_a is Phe, the benzene ring thereof is preferably unsubstituted.

When A comprises a Pro amino acid residue, any substituent present on the proline ring, e.g. R₃—NH—CO—O— etc., is preferably in position 4. Such substituted praline residue may exist in the cis form, e.g.

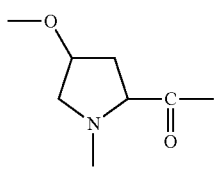

as well as in the trans form. Each geometric isomer individually as well as mixtures thereof are compounds of the invention.

When A is

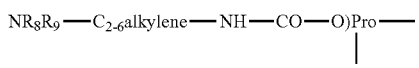

where $NR_8R_9$ forms a heterocyclic group, such group may be aromatic or saturated and may comprise one nitrogen or one nitrogen and a second heteroatom selected from nitrogen and oxygen. Preferably the heterocyclic group is e.g. pyridyl or morpholino. $C_{2-6}$ Alkylene in this residue is preferably —$CH_2$—$CH_2$—.

Any acyl as $R_5$, $R_6$, $R_8$ and $R_9$ in A may be e.g. $R_{12}CO$— wherein $R_{12}$ is H, $C_{1-4}$-alkyl, $C_{2-4}$alkenyl, $C_{3-6}$cycloalkyl or benzyl, preferably methyl or ethyl. When $R_{4a}$ or $R_{11}$ in A is ring-substituted benzyl, the benzene ring may be substituted as indicated above for $ZZ_a$.

Particularly preferred are compounds of formula III

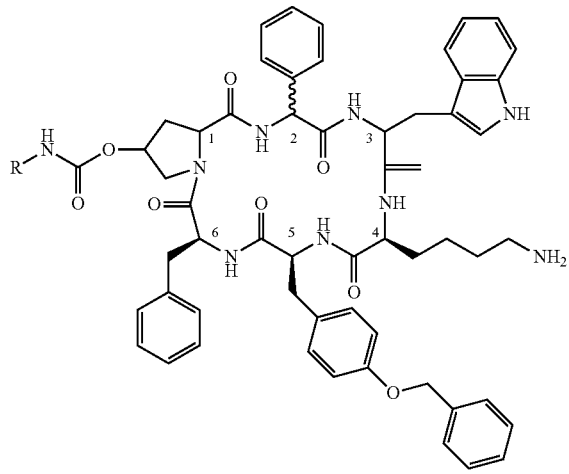

wherein the configuration at C-2 is (R) or (S) or a mixture thereof, and
wherein R is $NR_{10}R_{11}$—$C_{2-6}$alkytene or guanidine-$C_{2-6}$alkylene, and each of $R_{10}$ and $R_{11}$ independently is H or $C_4$alkyl, in free form, in salt form or protected form the synthesis of which may be performed as described e.g. in WO 2002/10192 which is hereby incorporated by reference, The salts are obtained by the process as described e.g. in WO 2002/10192 which is hereby incorporated by reference.

Preferably R is $NR_{10}R_{11}$—$C_{2-6}$alkylene. Preferred compounds of formula II are the compounds wherein R is 2-amino-ethyl, namely cyclo[{4-($NH_2$—$C_2H_4$—NH—CO—O—)Pro}-Phg-DTrp-Lys-Tyr(4-Bzl)-Phe](referred herein to as Compound A) and cyclo[{4-($NH_2$—$C_2H_4$—NH—CO—O—)Pro}-DPhg-DTrp-Lys-Tyr(4-Bzl)-Phe], In free form, salt form or protected form. Phg means —HN—CH($C_6H_5$)—CO— and Bzl means benzyl.

A salt of the invention in protected form corresponds to a somatostatin analogue wherein at least one of the amino groups is protected and which by deprotection leads to a compound of formula II, preferably physiologically removable. Suitable amino protecting groups are e.g. as disclosed in "Protective Groups in Organic Synthesis", T. W, Greene, J. Wiley & Sons NY (1981), 219-287, the contents of which being incorporated herein by reference. Example of such an amino protecting group is acetyl.

The composition according to the present invention may comprise a buffer. Suitable buffers include but are not limited to acetate buffer, lactate buffer, glycin buffer and tartrate buffer. The concentrations of the buffers may be from about 5 mM to 30 mM, preferably from about 10 mM to 25 mM.

In a further aspect the invention provides a pharmaceutical composition in a viscous liquid form that may be injected with a syringe through a needle ranging from 18 G to 25 G, e.g. 20 G. The solution may be placed in a syringe after sterile filtration through a 0.2 μm filter having a viscosity of from 1 to 10 mPa·s or after sterile filtration and solvent removal by evaporation or sublimation having a viscosity of from $10^2$ to $10^8$ mPa·s. The solvent removal may be done after placing the solution in the syringe.

The solution in the syringe may be injected through a needle, e.g. a 20 G needle, into the body subcutaneously, intramuscularly, intradermally or intraperitoneally or placed into accessible tissue sites through a cannula. Once in place in contact with the patient's body fluid the gelling depot will be formed. The liquid composition for parenteral administration may be filled in a syringe, preferably a prefilled syringe may be provided together with instructions for use.

In another aspect the invention provides a depot formulation for extended release of the pharmaceutically active agent. The implant formed after injection into the body may release the active agent over an extended period of time. The release period may range from 1 up to 90 days, e.g. 1 up to 60 days, e.g. between 30 to 60 days.

The compositions of the invention are useful for treatment of the known indications of the particular active agent. Compositions of the invention comprising a somatostatin analogue salt of aspartate, lactate, succinate, acetate, glutamate or citrate may be useful in the following indications:
a) for the prevention or treatment of disorders with an aetiology comprising or associated with excess GH-secretion and/or excess of IGF-1 e.g. in the treatment of acromegaly as well as in the treatment of type I or type II diabetes, mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity,
b) in the treatment of enterocutaneous and pancreaticocutaneous fistula, irritable bowel syndrom, inflammatory diseases, e.g. Grave's Disease, inflammatory bowel disease, psoriasis or rheumatoid arthritis, polycystic kidney disease, dumping syndrom, watery diarrhea syndrom, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding, c) for the prevention or treatment of angiogenesis, inflammatory disorders as indicated above including inflammatory eye diseases, macular edema, e.g. cystoid macular edema, idiopathic cystoid macular edema, exudative age-related macular degeneration, choroidal neovascularization related disorders and proliferative retinopathy, d) for preventing or combating graft vessel diseases, e.g. allo- or xenotransplant vasculopathies, e.g. graft vessel atherosclerosis, e.g. in a transplant of organ, e.g. heart, lung, combined heart-lung, liver, kidney or pancreatic transplants, or for preventing or treating vein graft stenosis, restenosis and/or vascular occlusion following vascular injury, e.g. caused by catherization procedures or vascular scraping procedures such as percutaneous transluminal angioplasty, laser treatment or other invasive procedures which disrupt the integrity of the vascular intima or endothelium, e) for treating somatostatin receptor expressing or accumulating tumors such as pituitary tumors, e.g. Cushing's Disease, gastro-enteropancreatic, carcinoids, central nervous system, breast, prostatic (including advanced hormone-refractory prostate cancer), ovarian or colonic tumors, small cell lung cancer, malignant bowel obstruction, paragangliomas, kidney cancer, skin cancer, neuroblastomas, pheochromocytomas, medullary thyroid carcinomas, myelomas, lymphomas, Hodgkins and non-Hodgkins lymphomas, bone tumours and metastases thereof, as well as autoimmune or inflammatory disorders, e.g. rheumatoid arthritis, Graves disease or other inflammatory eye diseases.

Preferably, the compositions of the invention are useful in the treatment of acromegaly, carcinoids and/or Cushing's Disease.

The activity and the characteristics of the liquid compositions of the invention may be indicated in standard clinical or animal tests.

Appropriate dosage of the composition of the invention will of course vary. e.g. depending on the condition to be treated (for example the disease type of the nature of resistance), the drug used, the effect desired and the mode of administration.

For compositions of the invention comprising the somatostatin salt of aspartate, lactate, succinate, acetate, glutamate or citrate satisfactory results are obtained on administration, e.g. parenteral administration, at dosages in the order of from about 0.1 to about 100 mg, preferably from about 3 to about 60 mg per injection per month or about 0.01 to about 4 mg preferably 0.1 to 1 mg per kg animal body weight per month, administered once or in divided doses. Suitable monthly dosages for patients are thus in the order of about 0.1 mg to about 80 mg of a somatostatin analogue salt of aspartate, lactate, succinate, acetate, glutamate or citrate.

The present invention provides a simple pharmaceutical composition of somatostatin analogue salt of aspartate, e.g. mono- or diaspartate, lactate, succinate e.g. mono- or disuccinate, acetate, glutamate, e.g. mono- or diglutamate, or citrate in a salt:base ratio ranging from 0.1 to 2 and water at a defined pH between 3.0 to 7.0, preferably between about 4.0 to 6.0, more preferably between about 4.0 to 5.0. The salt base ratio ranging from 0.1 to 2 provides the solubility of the somatostatin analogue salt at a given pH and the precipitation and depot formation after contact with body fluids and therefore environmental pH change. The pH may be stabilized by a buffer. The process to prepare the composition is simple by adding water to the somatostatin analogue salt. At a pH between about 4.0 to 6.0 the composition shows good solubility and therefore precipitation, e.g. in a prefilled, syringe or needle clogging is avoided. No organic solvents that might cause severe side effects at the place of administration are used.

Following is a description by way of example only of processes and compositions of the invention.

EXAMPLE 1

| Raw materiels | Weight g | Required weight | Actual weight |
|---|---|---|---|
| Somatostatin diaspartate | 58.8235 | 0.8 g | 0.8 g |
| Water for injection (WFI) | 100 | 1.36 ml | 1.36 ml |

A 2 ml solution of the pharmaceutical composition of the present invention is made by mixing 0.8 g somatostatin diaspartate with 1.36 ml water for injection. The release profile in rabbits of the drug product having the composition given in Example 1, is illustrated in FIG. 1. The composition has been injected parenterally and blood samples have been taken several times during a period of 2 months to measure the somatostatin diaspartate.

EXAMPLE 2

| Raw materiels | Required weight | Actual weight |
|---|---|---|
| Somatostatin di-succinate | 1.0 g | 0.999 g |
| Water for injection (WFI) | 1.6 ml | 1.6 ml |

The di-succinate form of the pharmaceutical composition of the present invention is made by mixing 0.999 g somatostatin di-succinate with 1.6 ml water for injection.

EXAMPLE 3

| Raw materiels | Required weight | Actual weight |
|---|---|---|
| Somatostatin di-glutamate | 0.916 g | 0.916 g |
| Water for injection (WFI) | 1.44 ml | 1.44 ml |

Figure 2:
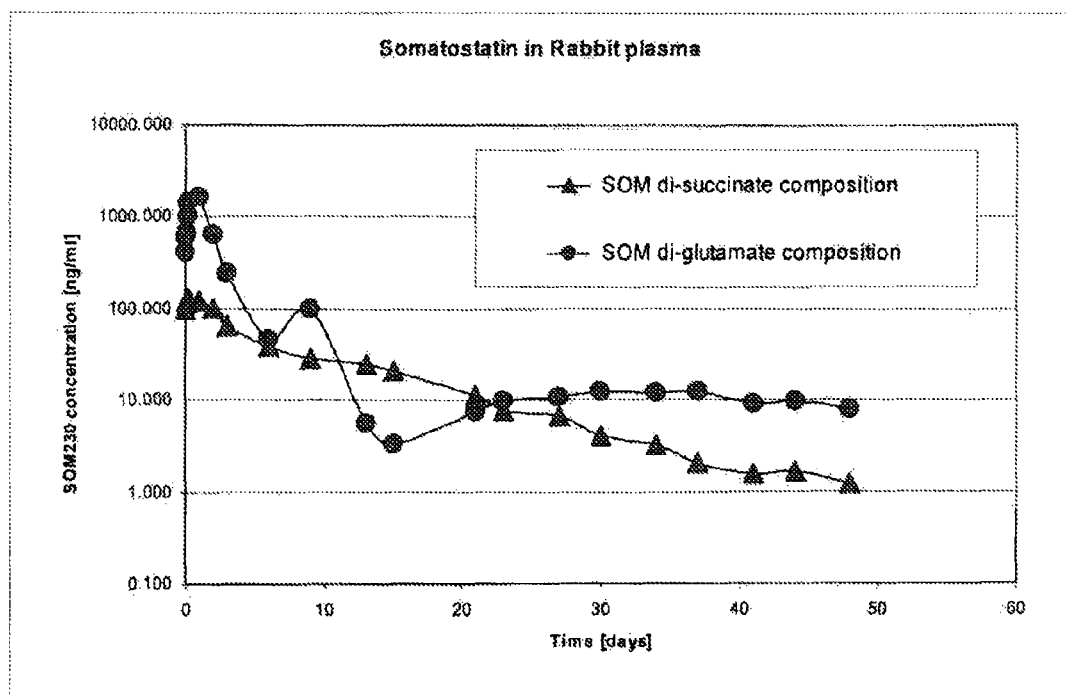
FIG. 2 shows release profile in rabbits of the drug product having the composition given in example 2 and 3.

The di-glutamate form of the pharmaceutical composition of the present invention is made by mixing 0.916 g somatostatin di-glutamate with 1.44 ml water for injection. The release profile in rabbits of the drug product having the composition given in example 2 and 3, is illustrated in FIG. 2. The composition has been injected parenterally and blood samples have been taken several times during a period of 2 months to measure the somatostatin disuccinate and somatostatin diglutamate.

The invention claimed is:

1. A liquid pharmaceutical composition for parenteral administration comprising a lactate, acetate, diaspartate, diglutamate, or discuccinate salt of a somatostatin analogue cyclo[{4-NH$_2$—C$_2$H$_4$NH—CO—O—)Pro}-Phg-DTrp-Lys-Tyr(4-Bzl)-Phe] and water forming a gelling depot system after injection in contact with body fluid.

2. The liquid pharmaceutical composition of claim 1 having a pH of between 3.0 and 7.0.

3. The liquid pharmaceutical composition of claim 1 wherein the somatostatin analogue salt has a salt:base ratio ranging from 0.1 to 2.

4. The liquid pharmaceutical composition according to claim 1 having a pH of between about 4.0 and 6.0.

5. The liquid pharmaceutical composition according to claim 1 having a pH of between about 4.0 and 5.0.

6. The liquid pharmaceutical composition according to claim 1 comprising a pharmaceutically acceptable buffer in an amount to provide a pH of between about 3 and 7.

7. The liquid pharmaceutical composition according to claim 6 having a pH of between about 4.0 and 5.0.

8. The liquid pharmaceutical composition according to claim 6 wherein the pharmaceutically acceptable buffer is chosen from at least one of an acetate buffer, a tartrate buffer, a glycin buffer and a lactate buffer.

9. The liguid pharmaceutical composition according to claim 6 wherein the pharmaceutically acceptable buffer is acetate buffer.

10. The liquid pharmaceutical composition according to claim 9 wherein the acetate buffer is used in a concentration of about 10 mM to 25 mM.

11. The liquid pharmaceutical composition according to claim 1 wherein said gelling depot system releases somatostatin analogue salt of diaspartate, lactate, disuccinate, acetate, or diglutamate continuously within the patient over an extended period of time of from 1 to 90 days.

12. The liquid pharmaceutical composition of claim 11 wherein said gelling depot system releases somatostatin analogue salt of diaspartate, lactate, disuccinate, acetate, or diglutamate continuously within the patient over an extended period of time of from 1 to 60 days.

13. The liquid pharmaceutical composition according to claim 1 having a viscosity from 1 to $10^6$ mPa·s.

14. A prefilled syringe comprising the liquid composition of claim 1 and instructions to use.

15. A process to prepare the liquid pharmaceutical composition according to claim 1 comprising
   i) dissolving a somatostatin analogue salt lactate, acetate, diaspartate, diglutamate, or discuccinate in water,
   ii) optionally adding a pharmaceutically acceptable amount of a buffer, and optionally
   iii) filling the solution into a syringe.

16. A process to prepare the liquid pharmaceutical composition according to claim 1 comprising
   iv) dissolving a somatostatin analogue salt of lactate, acetate, diaspartate, diglutamate, or discuccinate in water,
   v) adding a pharmaceutically acceptable amount of a buffer to obtain a pH of between 3.0 and 7.0, and optionally
   vi) filling the solution into a syringe.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Somatostatin tetradecapeptide

<400> SEQUENCE: 1

Ala Gly Cys Lys Asn Phe Phe Trp Lys Thr Phe Thr Ser Cys
1               5                   10